United States Patent
Pelletier et al.

(10) Patent No.: US 10,085,933 B2
(45) Date of Patent: *Oct. 2, 2018

(54) **COSMETIC USE OF AN ESSENTIAL OIL OF *LASERPITIUM SILER* L. FOR KERATIN MATERIALS**

(71) Applicant: L'OREAL, Paris (FR)

(72) Inventors: Pascale Pelletier, Antony (FR); Agnès Pegeon, Meudon (FR); Pierre Lartaud, Eurre (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,492

(22) PCT Filed: Dec. 16, 2014

(86) PCT No.: PCT/IB2014/066957
§ 371 (c)(1),
(2) Date: Jun. 20, 2016

(87) PCT Pub. No.: WO2015/092673
PCT Pub. Date: Jun. 25, 2015

(65) Prior Publication Data
US 2016/0331674 A1    Nov. 17, 2016

(30) Foreign Application Priority Data
Dec. 20, 2013    (FR) ...................................... 13 63294

(51) Int. Cl.
A61K 8/92       (2006.01)
A61Q 7/00       (2006.01)
A61Q 19/00      (2006.01)
A61Q 19/06      (2006.01)
A61Q 19/08      (2006.01)
A61K 36/23      (2006.01)

(52) U.S. Cl.
CPC .............. *A61K 8/922* (2013.01); *A61K 36/23* (2013.01); *A61Q 7/00* (2013.01); *A61Q 19/001* (2013.01); *A61Q 19/06* (2013.01); *A61Q 19/08* (2013.01); *A61K 2800/805* (2013.01)

(58) Field of Classification Search
None
See application file for complete search history.

(56) References Cited

U.S. PATENT DOCUMENTS 5,571,794 A    11/1996    Frome

FOREIGN PATENT DOCUMENTS

| EP | 916 652 A1 | 5/1999 |
|---|---|---|
| FR | 2883167 A1 | 9/2006 |
| FR | 2949674 A1 | 3/2011 |
| FR | 2994527 A1 | 2/2014 |
| FR | 2994528 A1 | 2/2014 |
| FR | 2994529 A1 | 2/2014 |
| JP | H02-295912 A | 12/1990 |
| JP | 2004-010526 A | 1/2004 |
| WO | 97/32562 A1 | 9/1997 |
| WO | 98/05654 A1 | 2/1998 |
| WO | 00/59866 A1 | 10/2000 |
| WO | 03/072039 A2 | 9/2003 |
| WO | 2011/101239 A2 | 8/2011 |
| WO | WO 2011/101239 * | 8/2011 |
| WO | 2014/030117 A2 | 2/2014 |

OTHER PUBLICATIONS

Tirillini et al., "Chemical Composition and Fungicidal Activity of the Essential Oil of Laserpitium garganicum from Italy", Chemistry of Natural Compounds, 45(1), 2009, pp. 103-105.*
Bo Jensen; "Laserwort-Laserpitium siler (Umbelliferae/Apiaceae)"; Internet Citation; Apr. 26, 2012; http://wayback.archive.org/web/20120426092119/http://bojensen.net/EssentialOilsEng/EssentialOils15/EssentialOils15.htm.
Lechner et al; "Antimycobacterial Activity of *Laserpitium silver* L. Roots;" Supplement 1; Sci. Pharm.; vol. 74; 2006; p. S 94.
May 7, 2015 Search Report issued in International Patent Application No. PCT/IB2014/066957.
May 7, 2015 Written Opinion issued in International Patent Application No. PCT/IB2014/066957.

* cited by examiner

*Primary Examiner* — Melissa L Fisher
(74) *Attorney, Agent, or Firm* — Oliff PLC

(57) ABSTRACT

The present invention relates to the cosmetic use of an essential oil of *Laserpitium siler* L., as an active agent for preventing and/or treating skin or keratin disorders associated with constriction of the cutaneous capillary circulation. The invention is also directed towards the cosmetic use of the said essential oil as an active agent for improving the appearance of the lips by increasing the size and/or volume and/or thickness of the lips and/or for (re)modelling them and/or making them smooth, and also to a non-therapeutic cosmetic process for caring for the skin and/or keratin fibers.

13 Claims, No Drawings

COSMETIC USE OF AN ESSENTIAL OIL OF *LASERPITIUM SILER* L. FOR KERATIN MATERIALS

The present invention relates to the field of cosmetic products, more particularly intended for caring for keratin materials, in particular the skin and/or the hair.

More particularly, the present invention is directed towards proposing the use of a novel active agent for preventing and/or treating skin or keratin disorders associated with constriction of the cutaneous capillary circulation.

The present invention is also directed towards the cosmetic use of a novel active agent for improving the appearance of the lips by increasing the size and/or volume and/or thickness of the lips and/or for (re)modelling them and/or making them smooth. The invention also relates to a non-therapeutic cosmetic process for caring for the skin and/or keratin fibres, comprising the topical application to the said skin and/or to the said keratin fibres of a composition comprising the said active agent.

The term "skin" means the entire skin of the body, including the lips, the scalp and mucous membranes.

The term "keratin fibres" more particularly means human keratin fibres such as the hair, the eyelashes and the eyebrows.

The skin is the largest organ of the human body, and its surface area represents 1.8 $m^2$ on average in adults for a thickness of 1 to 3 mm.

Like any organ, the skin has a circulatory system, which, on account of its dimensions, is a capillary circulatory system. This system is an organization of relatively undifferentiated and relatively strong vessels, the architecture of which is well defined only in the vicinity of the epithelia.

The role of the cutaneous capillary circulation is more important than the simple nutrition of the organ and the removal of waste derived from its metabolism.

Specifically, the capillary circulation is directly involved in heat regulation (dispersion of the intrinsic heat) and in protecting the body against numerous attacking factors.

Furthermore, the cutaneous capillary circulation participates in maintaining the homeostasis of the internal environment, and in maintaining the arterial pressure and the water balance of the body.

Constriction of the cutaneous capillary circulation may be associated with certain skin or keratin disorders in particular such as cellulite, slackening of the skin and hair loss.

As regards cellulite, it is generally defined as a hydrolipodystrophy, i.e. an infiltration of water and an accumulation of fat, leading to thickening and disorganization of the fibrous tissue.

Added to these manifestations is the compression of the blood and lymphatic vessels, which results in a slowing-down of the exchanges, which may lead to a state of "asphyxia" of the connective tissue.

Cellulite is generally found in women, but also, albeit more rarely, in men.

In women, usually, most of the fat is located in the bottom half of the body, below the horizontal plane passing through the navel (gluteal and femoral fat giving the deposits well known as saddlebags), whereas, in men, fat is preferentially concentrated on the top half of the body, above this same plane.

Cellulite is clinically manifested by an "orange peel" appearance, since the skin surface becomes irregular of flaccid or gelatinous consistency and is often associated with slackening of the skin.

In particular given the profound physical and aesthetic, and occasionally psychological, discomfort that cellulite may elicit in individuals suffering therefrom, it nowadays constitutes a condition that is increasingly poorly tolerated or accepted.

Various techniques such as laser lipolysis, liposculpture, liposuction, unipolar, bipolar or multipolar radiofrequency treatment, for instance the "skin surfing" technique, and manual lymphatic draining or the exploration of biological pathways acting on the mechanism of lipogenesis and/or of lipolysis are well known for treating cellulite.

However, most of these techniques are expensive and restrictive.

As regards the hair loss, it is known that, in humans, the growth and renewal of hair is mainly determined by the activity of the hair follicles and of their cutaneous and/or connective-tissue environment. Their activity is cyclical and essentially comprises three phases, namely the anagenic phase, the catagenic phase and the telogenic phase.

The active anagenic phase or growth phase, which may last several years and during which the hairs lengthen, is followed by a very short and transient catagenic phase which lasts a few weeks. During this phase, the hair undergoes involution, the follicle becomes atrophied and its dermal implantation appears increasingly higher.

The terminal phase, known as the telogenic phase, which lasts a few months, corresponds to a resting period of the follicle, and the hair finishes by falling out. After this resting phase, a new follicle is regenerated, in place, and a new cycle begins.

The head of hair is thus in constant renewal, and, of the approximately 150 000 individual hairs that make up a head of hair, approximately 10% are at rest and will be thus replaced in the months to come. The natural loss of the hair can be estimated, on average, at a few hundred hairs per day for a normal physiological state. This constant physical renewal process undergoes a natural change during the course of ageing; the hairs become finer and their cycles shorter.

It is moreover known that various factors may lead to temporary or definitive loss of the hair.

It may be a case of loss and impairment of the hair in the end stage of a pregnancy (post-partum effluvium), in the course of states of malnutrition or of eating disorders, or alternatively in the course of asthenia or of hormonal dysfunction, as may be the case in the course or in the end stage of the menopause.

It may also be a case of loss or impairment of the hair in relation with seasonal phenomena.

It may also be a case of alopecia, which is essentially due to a disruption of hair renewal.

The term alopecia also covers an entire family of hair follicle complaints whose final consequence is partial or general definitive loss of the hair. It may more particularly be a case of androgenic alopecia.

Finally, hair loss in humans may also be the consequence of rarefaction of the vascular networks of the hair follicles.

For stimulating or inducing hair growth and/or stopping hair loss, patent application WO 97/32562 discloses N-aryl-2-hydroxyalkylamide compounds, patent application WO 98/05654 discloses 3-aryl-2,4-dioxooxazolidine compounds, patent application EP 916 652 discloses N-aryl-2-hydroxyalkylamide compounds, patent application WO 00/0 059 866 discloses benzoic acid ester derivatives, and patent application FR 2 883 167 discloses cosmetic compositions comprising a combination of 2,4-diaminopyrimidine 3-N- oxide and of a vasodilator and/or an amino acid. These compounds generally pose stability or solubility problems in the composition supports.

The inventors have discovered, unexpectedly, that a certain type of active agent specifically proves to be advantageous for preventing and/or treating the abovementioned disorders and in particular cellulite and hair loss via their beneficial effect with regard to the capillary circulation they stimulate. Moreover, the inventors have discovered that this stimulatory effect could also advantageously be exploited for intensifying or even increasing the volume of the lips or for making the lips voluptuous.

According to the invention, "making the lips voluptuous" means increasing the size and/or volume and/or thickness of the lips and/or remodelling them and/or making them smooth and/or giving them a more swollen or fleshy appearance.

Specifically, besides their exposure to external attacking factors (cold, heat, wind, dry air) and their submission to mechanical stresses (speech, expressions, food) and humid stresses (saliva, drinks), the lips may lose colour and/or volume on account of the rarefaction of the vascular networks.

This may result in a lack of firmness and the formation of fine lines in the region of the lips.

Admittedly, it is known practice to make the lips voluptuous via cosmetic surgery, injection or tattooing techniques, and the use of these techniques has tended to become generalized, including in the case of women with normal lips, who wish to have fleshy or pouty lips.

However, these techniques are expensive, may in certain cases give an irreversible result (e.g.: cosmetic surgery, tattooing) or may give rise to other side effects such as infection or allergy (e.g.: injection of collagen, tattooing).

Another alternative consists in applying to the lips certain active agents, for instance the beta-adrenergic receptor blockers or the muscarinic acetylcholine receptor activators described in patent U.S. Pat. No. 5,571,794, an L-arginine-based polymer described in patent application WO 03/072 039, or a neuropeptide Y (NPY) antagonist described in patent application FR 2 949 674. However, these agents are not entirely satisfactory.

Thus, there is an ongoing need for novel active agents that are capable of exerting a beneficial action on constriction of the cutaneous capillary circulation in order to exploit them, on the one hand to prevent and/or treat skin or keratin disorders associated with constriction of the cutaneous capillary circulation, and on the other hand to afford a particular aesthetic effect such as making the lips voluptuous.

Thus, there is a need for active agents and novel compositions that are effective in preventing and/or treating skin or keratin disorders associated with constriction of the cutaneous capillary circulation, and that are pleasant and comfortable to use, thus promoting adherence to the treatment.

Furthermore, there is a need for novel active agents for improving the appearance of the lips by increasing the size and/or volume and/or thickness of the lips and/or for (re) modelling them and/or making them smooth.

The object of the present invention is to meet these needs.

Thus, according to a first subject, the present invention relates to the cosmetic use of an essential oil of *Laserpitium siler* L., as an active agent for preventing and/or treating skin or keratin disorders associated with constriction of the cutaneous capillary circulation.

Still according to this first aspect, the present invention is also directed towards protecting the cosmetic use of an essential oil of *Laserpitium siler* L., for preventing and/or treating cellulite and/or slackening of the skin.

Also according to this first aspect, the present invention is directed towards protecting the cosmetic use of an essential oil of *Laserpitium siler* L. for inducing and/or stimulating the growth of keratin fibres and in particular the hair and/or for slowing down their loss and/or increasing their density.

According to another subject, the present invention relates to the cosmetic use of an essential oil of *Laserpitium siler* L. as an active agent for improving the appearance of the lips by increasing the size and/or volume and/or thickness of the lips and/or for (re)modelling them and/or making them smooth.

The present invention is also directed towards protecting a non-therapeutic cosmetic process for caring for the skin and/or keratin fibres, comprising at least one step of applying to the skin and/or the keratin fibres a composition comprising at least the essential oil of *Laserpitium siler* L.

The term "care" means a non-therapeutic care capable of producing an aesthetic effect without, however, preventing or correcting a dysfunction of the keratin materials.

According to the invention, the term "preventing" or "prevention" means reducing the risk of occurrence or slowing down the occurrence of a given phenomenon, namely, according to the present invention, the skin or skin keratin disorders associated with constriction of the cutaneous capillary circulation, such as cellulite, slackening of the skin, the increase in hair density and hair loss, and also the thinning and/or loss of colour of the lips.

A composition that is suitable for use in the invention, i.e. which is intended for implementing the invention, may be a cosmetic composition, and thus comprises a physiologically acceptable medium.

Essential Oil of *Laserpitium siler* L.

A composition that is suitable for use in the invention comprises essential oil of *Laserpitium siler* L.

*Laserpitium siler* L., also known as *Laser siler*, sermontain or mountain siler, is a plant belonging to the Apiacea family. It is a hardy plant 40 to 130 cm in height which bears an imposing umbel during the flowering season (July-August).

This plant is found in dry rocky and prairie areas of the semi-mountainous regions of southern Europe at an altitude of between 400 m and 2000 m. This plant is more particularly found in France, especially in the Jura, the Alps, the Cévennes, the Corbières and the Pyrenees and more particularly in the Vercors, the Gap region and the Briançon region.

According to the definition given in international standard ISO 9235 and adopted by the Commission of the European Pharmacopoeia, an essential oil is an odoriferous product generally of complex composition, obtained from a botanically defined plant raw material, either by steam distillation, or by dry distillation, or via an appropriate mechanical process without heating (cold pressing). The essential oil is generally separated from the aqueous phase via a physical process which does not result in any significant change in the composition.

Methods for Obtaining Essential Oils

The choice of technique depends mainly on the starting material: its original state and its characteristics, its actual nature. The "essential oil/plant starting material" yield may be extremely variable depending on the plant: 15 ppm to more than 20%. This choice conditions the characteristics of the essential oil, in particular viscosity, colour, solubility, volatility, richness or poorness in certain constituents.

Among the methods for obtaining an essential oil, mention may be made more particularly of steam distillation and dry distillation.

Steam distillation corresponds to the vaporization, in the presence of steam, of a sparingly water-miscible substance. The starting material is placed in contact with boiling water or steam in an alambic. The steam entrains the essential oil vapour, which is condensed in the condenser and recovered as a liquid phase in a Florentine vase (or essence jar), where the essential oil is separated from the water by settling. The aqueous distillate that remains after the steam distillation, once the separation of the essential oil has been performed, is known as the "aromatic water" or "hydrolate" or "distilled floral water".

Dry distillation consists in obtaining the essential oil by distillation of woods, barks or roots, without addition of water or steam, in a closed chamber designed so that the liquid is recovered at the bottom. Cade oil is the best known example of a product obtained in this way.

Preferably, an essential oil of *Laserpitium siler* L. according to the invention is prepared via the steam distillation method.

Physicochemical Characteristics

Essential oils are generally volatile and liquid at room temperature, which distinguishes them from "set" oils. They are more or less coloured and their density is generally less than that of water. They have a high refractive index and most of them deflect polarized light. They are liposoluble and soluble in the usual organic solvents, distillable with steam, and very sparingly soluble in water.

Plant Raw Materials

An essential oil of *Laserpitium siler* L. according to the invention may be prepared from any plant material derived from at least one *Laserpitium siler* L. cultivated in vivo or derived from in vitro cultivation.

The term "in vivo cultivation" means any cultivation of standard type, i.e. in soil in the open air or in a greenhouse, or alternatively without soil.

The term "in vitro cultivation" means all the techniques known to those skilled in the art for artificially obtaining a plant or a plant part. The selection pressure imposed by the physicochemical conditions during the growth of plant cells in vitro makes it possible to obtain a standardized plant material that is available throughout the year, in contrast with plants cultivated in vivo.

The essential oil of *Laserpitium siler* L. used in the present invention may be obtained from any plant material derived from this whole plant or from any part of this plant, for instance the leaves, stems, roots, flowers, petals, seeds, umbels, fruit and buds, which are in various states of dryness (dry, withered or fresh form).

Preferably, an essential oil of *Laserpitium siler* L. according to the invention is obtained from the leaves, umbels and/or fruit seeds of *Laserpitium siler* L., more preferentially from the leaves and/or umbels, especially from the seed-bearing umbels.

According to a preferred embodiment, an essential oil of *Laserpitium siler* L. according to the invention is obtained from the umbels and/or the seed-bearing umbels, and more preferentially from the seed-bearing umbels.

According to a preferred embodiment, an essential oil of *Laserpitium siler* L. according to the invention is obtained from the leaves.

Advantageously, the umbels or seeds may be predried and ground.

An essential oil in accordance with the invention may be prepared according to the techniques mentioned above.

As mentioned above, preferably, an essential oil in accordance with the invention is obtained according to the standard technique of steam distillation.

According to a preferred embodiment, an essential oil in accordance with the invention is obtained from leaves, preferably by means of a steam distillation process.

Advantageously, an essential oil according to the invention is obtained from the umbels of the fruit of *Laserpitium siler* L. by hydrodistillation or from the leaves by steam distillation on glass distillation apparatus (such as 4-liter Clevenger apparatus), such as the apparatus defined in the European Pharmacopoeia for the determination of the essential oil of a plant material.

Preferentially, the essential oil according to the invention is prepared from the seed-bearing umbels of *Laserpitium siler* L. by hydrodistillation.

Preferentially, the essential oil according to the invention is prepared from the leaves of *Laserpitium siler* L. by steam distillation.

According to the present invention, the essential oil of *Laserpitium siler* L. may be used in an amount sufficient for obtaining the desired effect, i.e. an amount sufficient for preventing and/or treating skin or keratin disorders associated with constriction of the cutaneous capillary circulation, such as cellulite and/or slackening of the skin, for inducing and/or stimulating the growth of keratin fibres and in particular of the hair, and/or for slowing down their loss and/or increasing their density, or for improving the appearance of the lips by increasing the size and/or volume and/or thickness of the lips.

Preferably, the essential oil of *Laserpitium siler* L. is used in a cosmetic composition in a content ranging from 0.0001% to 10% by weight, preferably from 0.001% to 1% by weight and most preferentially from 0.01% to 0.5% by weight relative to the total weight of the cosmetic composition.

The chemical composition of the essential oil of *Laserpitium siler* L. in accordance with the invention thus obtained may be analysed by standard techniques known to those skilled in the art, such as gas chromatography GC analysis, chromatographic analysis with flame ionization detection, known as GC-FID, or GC/MS analysis, which consists in using a mass spectrometer coupled to a gas chromatograph.

Advantageously, the essential oil of *Laserpitium siler* L. mainly contains limonene, perillaldehyde and chamazulene. These three compounds are well known.

Limonene, the empirical formula of which is $C_{10}H_{16}$, is a chiral terpene hydrocarbon. At room temperature, it is a colourless liquid with a fresh, clean, orange odour characteristic of citrus fruit. Limonene is generally present in the essential oil of *Laserpitium siler* L. in a content ranging from 40% to 80% by weight and preferably from 50% to 70% by weight relative to the total weight of the said essential oil.

Perillaldehyde or perilla aldehyde, the empirical formula of which is $C_{10}H_{14}O$, is a monoterpene comprising an aldehyde function. Perillaldehyde is generally present in the essential oil of *Laserpitium siler* L. in a content ranging from 15% to 40% by weight and preferably from 20% to 35% by weight relative to the total weight of the said essential oil.

Chamazulene is a blue-coloured sesquiterpene hydrocarbon. Chamazulene is generally present in the essential oil of *Laserpitium siler* L. in a content of less than or equal to 10% by weight and preferably less than or equal to 5% by weight relative to the total weight of the said essential oil.

An essential oil in accordance with the invention may be used as such, i.e. alone, or may be introduced into a composition, especially a cosmetic composition.

According to a first embodiment, the essential oil is obtained from the umbels and even more preferentially from the seed-bearing umbels.

According to this first embodiment, the essential oil of *Laserpitium siler* L. in accordance with the invention comprises an amount of limonene ranging from 40% to 80% by weight and preferably ranging from 50% to 70% by weight relative to the total weight of the said essential oil, an amount of perillaldehyde ranging from 15% to 40% by weight and preferably ranging from 20% to 35% by weight relative to the total weight of the said essential oil, and an amount of chamazulene of less than or equal to 10% and preferably less than or equal to 5% by weight relative to the total weight of the said essential oil.

According to a second embodiment, the essential oil is obtained from the leaves.

According to this second embodiment, the essential oil of *Laserpitium siler* L. according to the invention comprises at least 40% by weight, preferably at least 50% by weight and better still at least 65% by weight of monoterpenes chosen from limonene, myrcene, sabinene, γ-terpinene, para-cymene and α-pinene, and at least 5% by weight and preferably at least 15% by weight of sesquiterpenes chosen from chamazulene, germacrene D and trans-β-carophyllene.

Composition

The composition that is suitable for use in the invention is intended for cosmetic application.

According to a first embodiment of the invention, the essential oil of *Laserpitium siler* L. may be incorporated into a cosmetic composition for preventing and/or treating skin or keratin disorders associated with constriction of the cutaneous capillary circulation.

The said skin disorders are more particularly cellulite and slackening of the skin.

As regards the keratin disorders, they are more particularly loss of the hair and thinned hair.

As indicated previously, an essential oil of *Laserpitium siler* L. according to the present invention mainly contains limonene, perillaldehyde and chamazulene.

Thus, according to one embodiment, a cosmetic composition that is suitable for use in the invention comprises an essential oil of *Laserpitium siler* L. in accordance with the invention comprising an amount of limonene ranging from 40% to 80% by weight and preferably ranging from 50% to 70% by weight relative to the total weight of the said essential oil, an amount of perillaldehyde ranging from 15% to 40% by weight and preferably ranging from 20% to 35% by weight relative to the total weight of the said essential oil, and an amount of chamazulene of less than or equal to 10% and preferably less than or equal to 5% by weight relative to the total weight of the said essential oil.

Preferably, an essential oil according to the invention, when it is present in a composition, may be formulated in a physiologically acceptable medium.

The term "physiologically acceptable medium" means a medium that is compatible with all keratin materials such as the skin, the scalp, the nails, mucous membranes, the eyes and the hair, or any other area of bodily skin. A physiologically acceptable medium is preferentially a cosmetically acceptable medium, i.e. it is entirely compatible with the route of administration under consideration.

When the composition is intended to be administered topically, such a medium is considered as being physiologically acceptable when it does not cause any stinging, tautness or redness that is unacceptable to the user.

Advantageously, a composition that is suitable for use in the invention, comprising an essential oil of *Laserpitium siler* in accordance with the invention, is intended for topical administration.

A composition that is suitable for use in the invention may be in any galenical form normally used in the cosmetic field.

It may especially be in the form of an aqueous or aqueous-alcoholic solution, which is optionally gelled, a dispersion of the lotion type, which is optionally a two-phase lotion, an oil-in-water or water-in-oil or multiple emulsion, an aqueous gel, a gelled or non-gelled oil, a dispersion of oils in an aqueous phase, in particular with the aid of spherules, these spherules possibly being polymer particles or, better still, lipid vesicles of ionic and/or nonionic type, or alternatively in the form of a powder, a serum, a paste or a flexible stick. It may be of solid, pasty or more or less fluid liquid consistency.

It may thus be in the form of an ointment, a tincture, a cream, a pomade, a powder, a patch, an impregnated pad, a solution, an emulsion or vesicular dispersion, a lotion, a gel, a spray, a suspension, a shampoo, an aerosol or a foam. It may be anhydrous or aqueous. It may also consist of solid preparations constituting soaps or cleansing bars. These compositions are prepared according to the usual methods.

According to one variant of the invention, the compositions contain less than 5% by weight, in particular less than 3% by weight and more particularly less than 1% by weight of water, or even are free of water, i.e. anhydrous.

The composition that may be used according to the invention may in particular consist of a haircare composition, and especially a shampoo or a hair conditioner, in particular for twice-weekly or weekly application, a hairsetting lotion, a medicated lotion, a haircare lotion, for example for daily or twice-weekly application, a styling cream or gel, hair restructuring lotions, a mask, etc.

Thus, the composition may comprise any constituent usually used in the envisaged topical application and administration.

Mention may be made in particular of water, solvents, oils of mineral, animal and/or plant origin, in particular as detailed hereinbelow, waxes, especially as described hereinbelow, pigments, fillers, surfactants, thickeners, gelling agents and preserving agents, and mixtures thereof.

A composition suitable for the invention may also contain various adjuvants commonly used in the cosmetics field, such as sequestrants, odour absorbers, UV-screening agents, fragrances, matt-effect agents, and abrasive fillers or exfoliants, and mixtures thereof.

A composition that is suitable for use in the invention may advantageously comprise at least one additional active agent for treating skin or keratin disorders associated with constriction of the cutaneous capillary circulation and/or for improving the appearance of the lips and/or for (re)modelling the lips and/or for making the lips smooth.

In the context of the present invention, the term "additional active agent" means a compound which, by itself, i.e. not requiring the intervention of an external agent to activate it, has biological activity that may in particular be: vasodilators or vascular protective agents, glucose uptake inhibitors, inhibitors of the enzymes of fatty acid synthesis, lipolytic agents, firming active agents, agents for stimulating the synthesis of dermal or epidermal macromolecules and/or for preventing their degradation, moisturizers, calmatives or anti-irritants.

The term "vasodilator compound" means any active agent which promotes the process of cutaneous capillary circulation, especially 1) via stimulation of the vasodilation of the dermal blood vessels, and/or 2) via stimulation or maintenance of angiogenesis, and/or 3) via stimulation of cell proliferation, and/or 4) via stimulation of endothelial cell migration.

This vasodilator compound may be a simple or complex molecule, in molecular or polymeric form.

The additional active agent used in the composition that is suitable for use in the invention may represent from 0.0001% to 20%, preferably from 0.01% to 10% and even better still from 0.01% to 5% by weight relative to the total weight of the composition.

Moreover, a composition suitable for the invention may advantageously comprise from 5% to 80% by weight and preferably from 35% to 75% by weight of water relative to the total weight of said composition.

Needless to say, those skilled in the art will take care to select this or these optional additional compound(s), and/or the amount thereof, such that the advantageous properties of the essential oil according to the invention are not, or are not substantially, adversely affected by the envisaged addition, and such that the properties of the compositions resulting therefrom are compatible with the preferred route of administration.

A composition that is suitable for use in the invention may advantageously comprise at least one fatty phase that is liquid at room temperature and atmospheric pressure.

As examples of oils that may be used in the composition that is suitable for use in the invention, mention may be made of:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;

synthetic esters and ethers, especially of fatty acids, for instance the oils of formulae $R_1COOR_2$ and $R_1OR_2$ in which $R_1$ represents a fatty acid residue containing from 8 to 29 carbon atoms and $R_2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, isohexadecane, isododecane, petroleum jelly, polydecenes, and hydrogenated polyisobutene such as Parleam® oil;

other related natural or synthetic essential oils;

fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, for instance those described in document JP-A-2 295 912;

silicone oils, for instance volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane and cyclopentasiloxane; polydimethylsiloxanes comprising alkyl, alkoxy or phenyl groups, which are pendent or at the end of a silicone chain, these groups containing from 2 to 24 carbon atoms; phenylsilicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; and mixtures thereof.

In the list of the abovementioned oils, the term "hydrocarbon-based oil" means any oil predominantly comprising carbon and hydrogen atoms, and optionally ester, ether, fluoro, carboxylic acid and/or alcohol groups.

The other fatty substances that may be present in the oily phase are, for example, waxes and fatty acids comprising from 8 to 30 carbon atoms, for instance stearic acid, lauric acid, palmitic acid and oleic acid.

As waxes that may be used according to the invention, mention may be made of waxes of animal origin such as beeswax, spermaceti, lanolin wax and lanolin derivatives, plant waxes such as carnauba wax, candelilla wax, ouricury wax, Japan wax, cocoa butter, cork fibre wax or sugarcane wax, mineral waxes, for example paraffin wax, petroleum jelly wax, lignite wax or microcrystalline waxes or ozokerites, synthetic waxes, among which are polyethylene waxes, polytetrafluoroethylene waxes and the waxes obtained by Fisher-Tropsch synthesis or alternatively silicone waxes, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., for instance the $C_{20}$-$C_{40}$ alkyl stearate sold under the trade name Kester Wax K82H by the company Koster Keunen.

These fatty substances may be chosen in a varied manner by a person skilled in the art so as to prepare a composition having the desired properties, for example in terms of consistency or texture.

The compositions suitable for the invention may comprise a volatile oil.

For the purposes of the invention, the term "volatile oil" means an oil that is capable of evaporating on contact with the keratin materials in less than one hour, at room temperature and atmospheric pressure. The volatile organic solvent(s) and volatile oils of the invention are volatile organic solvents and cosmetic oils that are liquid at room temperature, with a non-zero vapour pressure at room temperature and atmospheric pressure, ranging in particular from 0.13 Pa to 40 000 Pa (10-3 to 300 mmHg), in particular ranging from 1.3 Pa to 13 000 Pa (0.01 to 100 mmHg), and more particularly ranging from 1.3 Pa to 1300 Pa (0.01 to 10 mmHg).

Volatile oils that may be mentioned, inter alia, include linear or cyclic silicones containing from 2 to 6 silicon atoms, such as cyclohexasiloxane, dodecamethylpentasiloxane, decamethyltetrasiloxane, butyltrisiloxane and ethyltrisiloxane. It is also possible to use branched hydrocarbons, for instance isododecane, and also volatile perfluoroalkanes such as dodecafluoropentane and tetradecafluorohexane, sold under the names PF 5050® and PF 5060® by the company 3M, and perfluoromorpholine derivatives, such as 4-trifluoromethylperfluoromorpholine sold under the name PF 5052® by the company 3M.

The amount of oily phase present in the compositions suitable for the invention may range, for example, from 0.01% to 50% by weight and preferably from 0.1% to 30% by weight relative to the total weight of the composition.

A composition suitable for the invention may advantageously be in the form of an emulsion, obtained in particular by dispersing an aqueous phase in a fatty phase (W/O) or a fatty phase in an aqueous phase (O/W), of liquid or semi-liquid consistency of the milk type, or of soft, semi-solid or solid consistency of the cream or gel type, or alternatively a multiple emulsion (W/O/W or O/W/O). These compositions are prepared according to the usual methods.

Advantageously, when they are applied to the lips, the compositions that are suitable for use in the invention are anhydrous and comprise waxes and/or oils. Thus, they may be in the form of gels or creams.

Advantageously, for their slimming application, the compositions that are suitable for use in the invention are mainly in the form of aqueous-alcoholic gels or light emulsions, or alternatively in the form of massage oils.

Advantageously, for their application in preventing hair loss, the compositions that are suitable for use in the invention are essentially in the form of haircare gels, lotions, massage oils or creams.

A composition of this type may be in the form of a face and/or body care or makeup product, and may be conditioned, for example, in the form of cream in a jar or of fluid in a tube or a pump-action bottle.

The emulsions according to the invention may comprise at least one emulsifier chosen from amphoteric, anionic, cationic and nonionic emulsifiers, used alone or as a mixture.

Advantageously, the emulsifiers are appropriately chosen according to the emulsion to be obtained (W/O or O/W). The emulsifiers are generally present in the composition in a proportion that may range from 0.3% to 30% by weight and preferably from 0.5% to 20% by weight relative to the total weight of the composition.

Examples of emulsifiers that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

A composition according to the invention may also comprise at least one silicone elastomer, for instance the products sold under the name KSG by the company Shin-Etsu, under the name Trefil, BY29 or EPSX by the company Dow Corning, or under the name Gransil by the company Grant Industries.

A composition suitable for the invention may also comprise at least one colorant chosen, for example, from pigments, nacres, dyes and materials with an effect, and mixtures thereof.

These dyestuffs may be present in a content ranging from 0.01% to 50% by weight and preferably from 0.01% to 30% by weight relative to the total weight of the composition.

A composition suitable for the invention may also comprise at least one filler, in particular in a content ranging from 0.01% to 50% by weight and preferably ranging from 0.01% to 30% by weight relative to the total weight of the composition.

These fillers may be mineral or organic and of any shape, platelet-shaped, spherical or oblong, irrespective of the crystallographic form (for example lamellar, cubic, hexagonal, orthorhombic or amorphous).

Mention may be made of silica, talc, mica, kaolin, lauroyllysine, starch, boron nitride, PTFE powders, PMMA powders, methylsilsesquioxane resin powders (for instance Tospearl 145A from GE Silicone), hollow silicone resin hemispherical particles (for instance NLK 500, NLK 506 and NLK 510 from Takemoto Oil and Fat), barium sulfate, precipitated calcium carbonate, magnesium carbonate, magnesium hydrogen carbonate, hydroxyapatite, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myri state.

A composition that is suitable for use in the invention may be manufactured via any known process generally used in the cosmetic field.

The non-therapeutic cosmetic process of the invention is performed by topically administering a composition comprising an essential oil of *Laserpitium siler* L. in accordance with the invention.

The topical administration consists of the external application to the skin of cosmetic compositions according to the usual technique for using these compositions.

The non-therapeutic cosmetic treatment process according to the present invention is characterized in that the said essential oil is obtained from the leaves, umbels, seed-bearing umbels and/or fruit seeds of *Laserpitium siler* L.

According to a first embodiment, the essential oil is obtained from the umbels and even more preferentially from the seed-bearing umbels.

According to this particular embodiment, the said process is characterized in that the said essential oil of *Laserpitium siler* L. comprises an amount of limonene ranging from 40% to 80% by weight and preferably ranging from 50% to 70% by weight relative to the total weight of the said essential oil, an amount of perillaldehyde ranging from 15% to 40% by weight and preferably ranging from 20% to 35% by weight relative to the total weight of the said essential oil, and an amount of chamazulene of less than or equal to 10% and preferably less than or equal to 5% by weight relative to the total weight of the said essential oil.

According to a second embodiment, the essential oil is obtained from the leaves.

According to this second embodiment, the essential oil of *Laserpitium siler* L. according to the invention comprises at least 40%, preferably at least 50% by weight and better still at least 65% by weight of monoterpenes chosen from limonene, myrcene, sabinene, γ-terpinene, para-cymene and α-pinene, and at least 5% by weight and preferably at least 15% by weight of sesquiterpenes chosen from chamazulene, germacrene D and trans-β-carophyllene.

By way of illustration, the cosmetic process according to the invention may be performed by topical application, for example daily, of an essential oil of *Laserpitium siler* L. in accordance with the invention, which may, for example, be formulated in the form of creams, gels, sera, lotions, emulsions, balms, solutions, makeup-removing milks or aftersun compositions.

The process according to the invention may comprise a single application.

According to another embodiment, the application is repeated, for example 2 to 3 times daily for one day or more and generally for an extended period of at least 4 weeks, or even 4 to 15 weeks with, where appropriate, one or more periods of stoppage.

Furthermore, treatment combinations optionally with oral or topical forms may be envisaged, in order to complement or to reinforce the activity of the essential oil of *Laserpitium siler* L. as defined by the invention.

Thus, a topical treatment with a composition containing an essential oil of *Laserpitium siler* L. in accordance with the invention, combined with an orally or topically administered composition optionally containing another essential oil, could be imagined.

The ingredients are mixed, before being formed, in the order and under conditions that are easily determined by those skilled in the art.

According to a particular embodiment of the invention, other agents intended to make the appearance and/or the texture of the skin and/or of the keratin fibres, and more particularly the hair, more attractive may also be added to the composition that is suitable for use in the invention.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

The examples and figures that follow are presented as non-limiting illustrations of the invention. The compounds are, depending on the case, cited as the chemical names or as the CTFA names (*International Cosmetic Ingredient Dictionary and Handbook*).

EXAMPLES

Example 1: Production of an Essential Oil According to the Invention 0.1 kg of seed-bearing umbels of freshly harvested *Laserpitium siler* L. fruit is distilled, dried and flattened.

This distillation is performed for 180 minutes according to the steam distillation (or hydrodistillation) technique in "4-liter Clevenger" apparatus, i.e. apparatus based on the same principle as that detailed in the European Pharmacopoeia (PH. Eur. 4th Ed 2.8.12).

8 g of an essential oil according to the invention are thus obtained.

Chemical analysis of the composition of the essential oil thus obtained is performed by gas chromatographic GC analysis.

The results indicate that an essential oil of *Laserpitium siler* L. in accordance with the invention comprises as main compounds limonene (68.95%), perillaldehyde (23.79%) and chamazulene (1.49%).

Example 2: Production of an Essential Oil According to the Invention 0.3 kg of freshly harvested *Laserpitium siler* L. leaves are "fresh"-distilled without pretreatment.

This distillation is performed for 180 minutes according to the steam distillation technique in 4-liter Clevenger apparatus, i.e. apparatus based on the same principle as that detailed in the European Pharmacopoeia (PH. Eur. 4th Ed 2.8.12).

0.7 g of an essential oil according to the invention are thus obtained.

Chemical analysis of the composition of the essential oil thus obtained is performed by gas chromatographic GC analysis.

The results indicate that an essential oil of *Laserpitium siler* L. in accordance with the invention comprises as main compounds limonene (29.62%), myrcene (4.15%), sabinene (19.96%), γ-terpinene (2.12%), para-cymene (0.77%), α-pinene (12.17%), germacrene D (10.15%), chamazulene (5.29%) and trans-β-carophyllene (2.59%).

Example 3: Effect of the Essential Oil of *Laserpitium siler* L. According to Example 1 on Blood Vessel Dilation The object of this study is to analyse the effect on vascular modulation, namely vasodilation or vasoconstriction, of the essential oil of *Laserpitium siler* L. evaluated in a model of normal human skin maintained alive.

Calcitonin-gene related peptide (CGRP), which induces vasodilation, and noradrenalin, which induces vasoconstriction, are used as positive controls.

The analyses are histological by morphometric quantification of the calibre of the dermal capillaries and semi-quantitative evaluation of the oedema.

Materials and Methods

1) Model of Skin Maintained Alive

Fragments of normal human skin are obtained from a plastic surgery. They are placed in inserts, which are themselves positioned on culture wells. Culture medium specifically adapted to survival maintenance is added to the bottom of the wells, a passage being made by slow diffusion between the two compartments via a porous membrane (3 μm).

2) Preparation of Two Positive Controls (CGRP and Noradrenalin) and Application of the Essential Oil According to the Invention The first positive control consisted in preparing an experimental model of neurogenic inflammation by adding 5 μM CGRP to the culture medium so as to obtain vasodilation of the dermal capillaries.

The second positive control consisted in adding 1 μM noradrenalin to the culture medium so as to obtain vasoconstriction of the dermal capillaries.

The essential oil of *Laserpitium siler* L. at the test concentrations dissolved in ethanol is added to the culture medium.

The skin fragments are then maintained in organ culture for 48 hours in an oven under a humid atmosphere, at 37° C. and in the presence of 5% $CO_2$.

A comparative study is performed under the following conditions:
- control skin (unstimulated, untreated skin),
- skin stimulated with 1 µM noradrenalin,
- skin stimulated with 5 µM CGRP,
- skin treated with the product at the concentrations used.

3) Measurement of the Vascular Modulation

The skin fragments are fixed in Bouin liquid and included in paraffin. After staining with haemalum-eosin, two criteria are evaluated on the dermis: the oedema and the calibre of the capillaries.

a) Evaluation of the Modulation of the Calibre of the Capillaries

After staining with haemalum-eosin, the vascular dilation is evaluated by counting the number of dilated blood vessels on the entire histological slice (16 fields at magnification 40). This number is carried over to the total number of blood vessels in order to calculate the percentage of dilated vessels.

Moreover, a morphometric analysis of the area ($\mu m^2$) occupied by the lumen of the blood vessels was performed in order to determine the mean area ($\mu m^2$) occupied in the dermis by the vessels.

4) Statistical Analyses

A mean is calculated for each parameter from the results obtained on the six skin samples. The statistical analysis was performed via the "reduced deviation" Student test or paired-samples test, with a risk a of 5%.

Results

1) Evaluation of the Percentage of Dilated Vessels

The results concerning the overall percentage (%) of dilated capillaries are presented in the table below.

Histological Evaluation of the Percentage of Dilated Vessels

| | |
|---|---|
| control skin | 74.8 ± 20.8 |
| skin + CGRP | 90.5 ± 9.38 |
| | *p = 0.049 |
| skin + noradrenalin | 52.5 ± 20.6 |
| | *p = 0.047 |
| skin + essential oil of *Laserpitium siler* L. at 0.002% | 84.1 ± 8.8 |
| skin + essential oil of *Laserpitium siler* L. at 0.0002% | 81 ± 14.8 |

*statistically significant difference relative to the control skin (Student's paired test (p < 0.05))

CGRP induces a statistically significant increase in the number of dilated capillaries when compared with the control skin samples: 90.5% versus 74.8% (p=0.049).

Noradrenalin induces a statistically significant decrease in the number of dilated vessels when compared with the control skin samples: 52.5% versus 74.8% (p=0.047).

The essential oil of *Laserpitium siler* L. at the two concentrations, namely 0.002% and 0.0002%, increases the number of dilated vessels.

2) Measurement of the Mean Area of the Dilated Vessels

The results concerning the measurement of the mean area of the capillaries are given in the table below:

| | |
|---|---|
| control skin | 153.6 ± 74.4 |
| skin + CGRP | 242.7 ± 42.8 |
| | *p = 0.01 |
| skin + noradrenalin | 93.7 ± 65.7 |
| | *p = 0.04 |
| skin + essential oil of *Laserpitium siler* L. at 0.0002% | 229 ± 67.2 |
| | *p = 0.04 |

*statistically significant difference relative to the control skin (Student's paired test (p < 0.05))

The application of CGRP induces statistically significant vasodilation when compared with the control skin, with an area of 242.7 $\mu m^2$ versus 153.6 $\mu m^2$ (p=0.01).

Noradrenalin induces statistically significant vasoconstriction of the vessels when compared with the control skin samples, with an area of 93.7 $\mu m^2$ versus 153.6 $\mu m^2$ (p=0.04).

The essential oil of *Laserpitium siler* L. at 0.0002% induces statistically significant dilation of the area occupied by the capillaries in comparison with the control skin samples: 229 $\mu m^2$ versus 153.6 $\mu m^2$ (p=0.04).

The results obtained from these ex vivo tests confirmed that the essential oil of *Laserpitium siler* L. according to the invention significantly increases the dilation of the blood vessels.

Example 4: Compositions

Aqueous-Alcoholic Solution for Preventing Hair Loss

| Ingredients | Weight percentage relative to the total weight of the composition % |
|---|---|
| Oxyethylenated sorbitan monolaurate (20 OE) (Tween 20) | 0.5 |
| Ethanol | 21 |
| Essential oil of *Laser siler* L. of Example 1 | 0.1 |
| Water | qs 100 |

When applied to the hair and the scalp, this solution makes it possible to slow down hair loss.

Balm for Making the Lips Voluptuous

| Ingredients | Weight percentage relative to the total weight of the composition (%) |
|---|---|
| Beeswax | 11.3 |
| Shea butter | 6.3 |
| *Cocos nucifera* (coconut) oil bio BIO Kokosöl kbA VCO ® from Medwed & Werner | 1 |
| Decanoyl and octanoyl glyceride mixture Miglyol 812N from Cremer Oleo | 30.9 |
| Sunflower oil | 16 |
| Liquid lanolin Stellanol 10/40 from Stella | 34 |
| Mixture of natural α, β, γ and δ tocopherols (14/1/62/23) in sunflower oil (90/10) Covi-OX T 90 EU from Cognis/BASF | 0.4 |
| Essential oil of *Laser siler* L. of Example 1 | 0.1 |

When applied to the lips, this balm makes it possible to make the lips voluptuous.

Anti-Cellulite Gel

| Ingredients | Weight percentage relative to the total weight of the composition % |
| --- | --- |
| Glycerol | 3 |
| Water | qs 100 |
| Xanthan gum Rhodicare CFT from Rhodia | 0.8 |
| Cyclohexadimethylsiloxane Silsoft 1217 from Momentive Performance Materials | 10 |
| Water | 20 |
| Potassium sorbate | 0.5 |
| Propylene glycol | 3 |
| Essential oil of *Laser siler* L. of Example 1 | 0.1 |
| Ethyl alcohol | 20 |

When applied to bodily skin, this gel makes it possible to reduce cellulite.

The invention claimed is:

1. Cosmetic method for treating skin or keratin disorders associated with constriction of the cutaneous capillary circulation selected from the group consisting of cellulite, slacknening of the skin, hair loss, and thinned hair, and/or for inducing and/or stimulating the growth of keratin fibres and/or increasing their density, in a subject in need thereof, the method comprising topically applying to the skin or the keratin fibers of a subject in need thereof a composition comprising at least an essential oil of *Laserpitium siler* L, wherein the essential oil of *Laserpitium siler* L. comprises limonene in an amount ranging from 40% to 80% by weight relative to the total weight of said essential oil, perillaldehyde in an amount ranging from 15% to 40% by weight, relative to the total weight of said essential oil, and chamazulene in an amount of less than or equal to 10% by weight relative to the total weight of said essential oil.

2. Cosmetic method for improving the appearance of the lips by increasing the size and/or volume and/or thickness of the lips and/or making them smooth in a subject in need thereof, the method comprising topically applying to the lips of a subject in need thereof a composition comprising at least an essential oil of *Laserpitium siler* L, wherein the essential oil of *Laserpitium siler* L. comprises limonene in an amount ranging from 40% to 80% by weight relative to the total weight of said essential oil, perillaldehyde in an amount ranging from 15% to 40% by weight, relative to the total weight of said essential oil, and chamazulene in an amount of less than or equal to 10% by weight relative to the total weight of said essential oil.

3. Cosmetic method according to claim 1, wherein the said essential oil of *Laserpitium siler* L. is used in a cosmetic composition in a content ranging from 0.0001% to 10% by weight relative to the total weight of the cosmetic composition.

4. Cosmetic method according to claim 1, wherein the said essential oil is obtained from the umbels and/or from the fruit seeds and/or from the leaves of *Laserpitium siler* L.

5. Cosmetic method according to claim 4, wherein the said essential oil is obtained from the umbels.

6. Cosmetic method according to claim 4, wherein the said essential oil is obtained from the seed-bearing umbels.

7. Cosmetic method according to claim 4, wherein the said essential oil is obtained from the leaves.

8. Cosmetic method according to claim 1, wherein the said essential oil of *Laserpitium siler* L. comprises at least 40% by weight of monoterpenes selected from the group consisting of limonene, myrcene, sabinene, γ-terpinene, para-cymene and α-pinene, and at least 5% by weight of sesquiterpenes selected from the group consisting of chamazulene, germacrene D and trans-β-carophyllene.

9. Non-therapeutic cosmetic process for caring for the skin and/or keratin fibres, comprising at least one step of applying to the skin and/or the keratin fibres a composition comprising at least the essential oil of *Laserpitium siler* L., in which the said essential oil is obtained from the umbels and/or from the fruit seeds and/or from the leaves of *Laserpitium siler* L, wherein the essential oil of *Laserpitium siler* L. comprises limonene in an amount ranging from 40% to 80% by weight relative to the total weight of said essential oil, perillaldehyde in an amount ranging from 15% to 40% by weight, relative to the total weight of said essential oil, and chamazulene in an amount of less than or equal to 10% by weight relative to the total weight of said essential oil.

10. Non-therapeutic cosmetic process for caring for the skin and/or keratin fibres according to claim 9, in which the said essential oil is obtained from the umbels.

11. Non-therapeutic cosmetic process for caring for the skin and/or keratin fibres according to claim 9, in which the said essential oil is obtained from the seed-bearing umbels.

12. Non-therapeutic cosmetic process for caring for the skin and/or keratin fibres according to claim 9, in which the said essential oil is obtained from the leaves.

13. Non-therapeutic cosmetic process for caring for the skin and/or keratin fibres according to claim 9, in which the said essential oil comprises at least 40% by weight of monoterpenes selected from the group consisting of limonene, myrcene, sabinene, γ-terpinene, para-cymene and α-pinene, and at least 5% by weight of sesquiterpenes chosen from chamazulene, germacrene D and trans-β-carophyllene.

* * * * *